United States Patent [19]
Littleford

[11] 4,345,606
[45] * Aug. 24, 1982

[54] SPLIT SLEEVE INTRODUCERS FOR PACEMAKER ELECTRODES AND THE LIKE

[76] Inventor: Philip O. Littleford, 251 Salvador Sq., Winter Park, Fla. 32789

[*] Notice: The portion of the term of this patent subsequent to Sep. 4, 1996, has been disclaimed.

[21] Appl. No.: 133,325

[22] Filed: Mar. 24, 1980

Related U.S. Application Data

[60] Division of Ser. No. 9,137, Feb. 5, 1979, Pat. No. 4,243,050, which is a continuation-in-part of Ser. No. 860,246, Dec. 13, 1977, Pat. No. 4,166,469.

[51] Int. Cl.$^3$ .............................................. A61N 1/18
[52] U.S. Cl. .............................. 128/784; 128/214.4; 128/347; 128/419 P
[58] Field of Search .................. 128/214.4, 347, 348, 128/784–786, 419 P, 772, DIG. 9, 349

[56] References Cited

U.S. PATENT DOCUMENTS

| | | | |
|---|---|---|---|
| 3,348,544 | 10/1967 | Braun | 128/214.4 |
| 3,540,447 | 11/1970 | Howe | 128/347 |
| 3,570,485 | 3/1971 | Reilly | 128/214.4 |
| 3,628,524 | 12/1971 | Jamshidi | 128/347 X |
| 3,677,243 | 7/1972 | Nerz | 128/214.4 |
| 3,856,020 | 12/1974 | Kovac | 128/347 |
| 3,877,429 | 4/1975 | Rasumoff | 128/214.4 |
| 4,137,916 | 2/1979 | Killman et al. | 128/214.4 |

OTHER PUBLICATIONS

Vellani et al., "Endocardial Pacing . . . ", Brit. Heart J., 1969, 31, 106.
Friesen et al., "Percutaneous Insertion . . . Vein", The Can. J. Surg., Mar. 1977, 131–133, 135.

Primary Examiner—Lee S. Cohen
Attorney, Agent, or Firm—Duckworth, Allen, Dyer & Pettis

[57] ABSTRACT

An apparatus and related method for implanting pacemaker electrodes and similar devices within a patient include an introducer with a tapered end adapted to extend into the patient's body, and a hollow, tubular sleeve having a first portion with an inner dimension greater than the outer dimension of the introducer and a second portion at one end of the sleeve which extends parallel with the introducer and in close engagement therewith, with a gradual taper along the sleeve between the first and second portions. The sleeve has a longitudinal slit along the first portion and through the taper, but short of the forward extremity, to permit the sleeve to be peeled away from the pacemaker electrode after introduction. The introducer and sleeve include corresponding hub and flange arrangements which provide a means for locking the two elements together to prevent inadvertent motion of the sleeve with respect to the introducer as the two elements are being inserted into the patient. The flange on the sleeve has a dimension extending away from the sleeve sufficient to permit the physician to place his thumb over the open extremity of the sleeve to prevent air aspiration into the patient.

10 Claims, 24 Drawing Figures

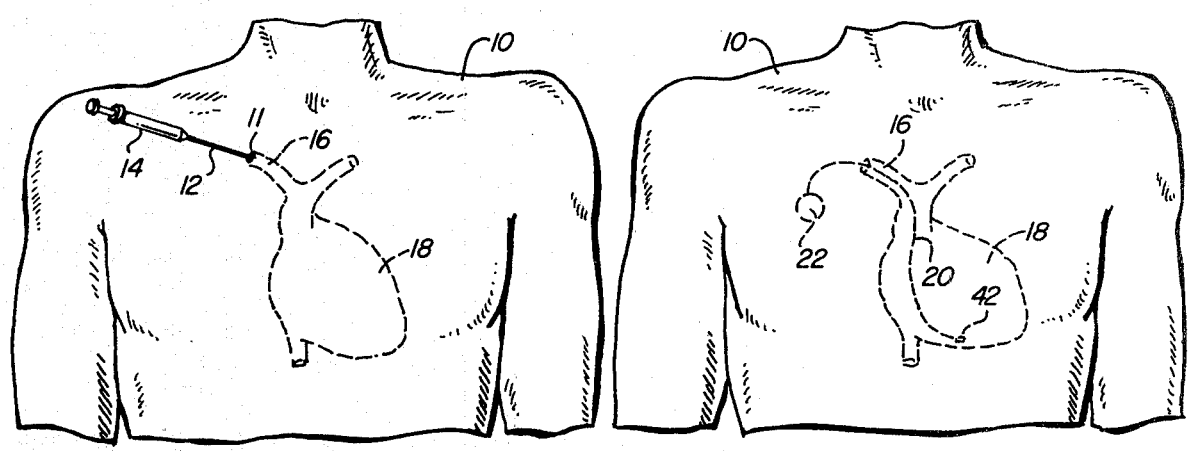
FIG-1  FIG-2
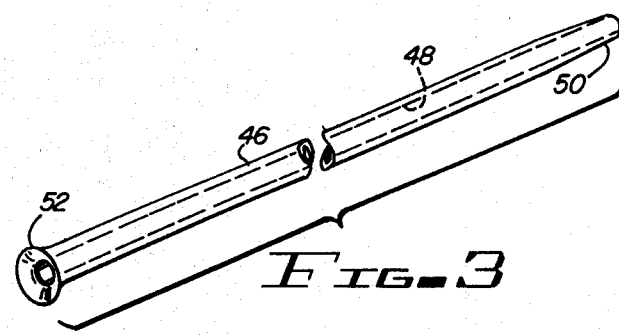  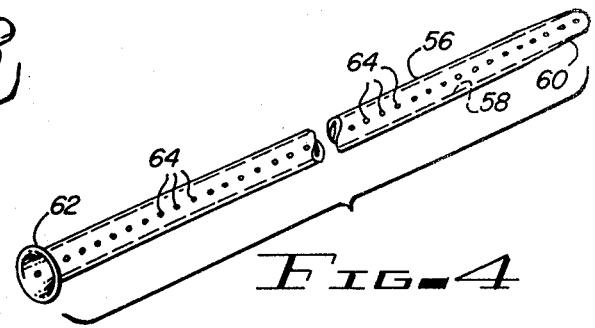
FIG-3  FIG-4
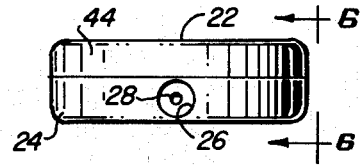
FIG-5
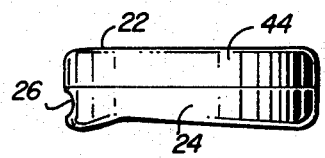
FIG-6
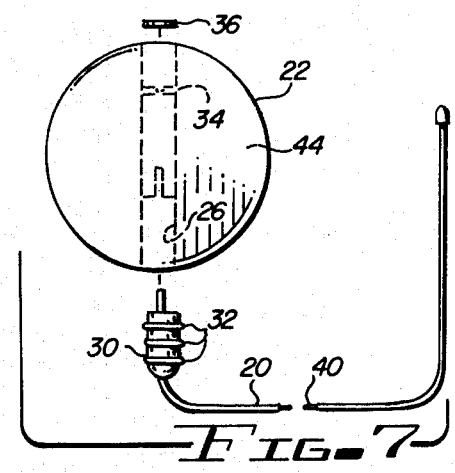
FIG-7
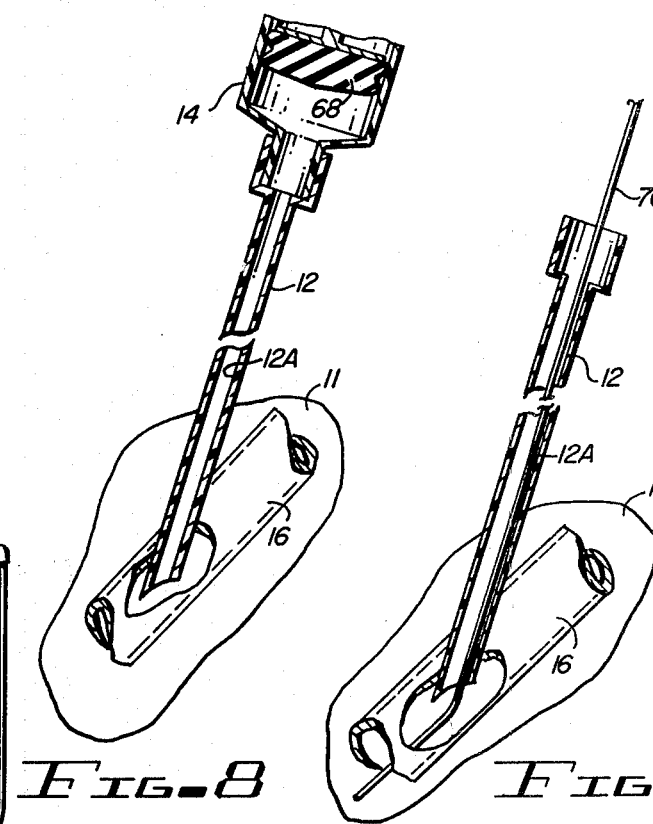
FIG-8  FIG-9

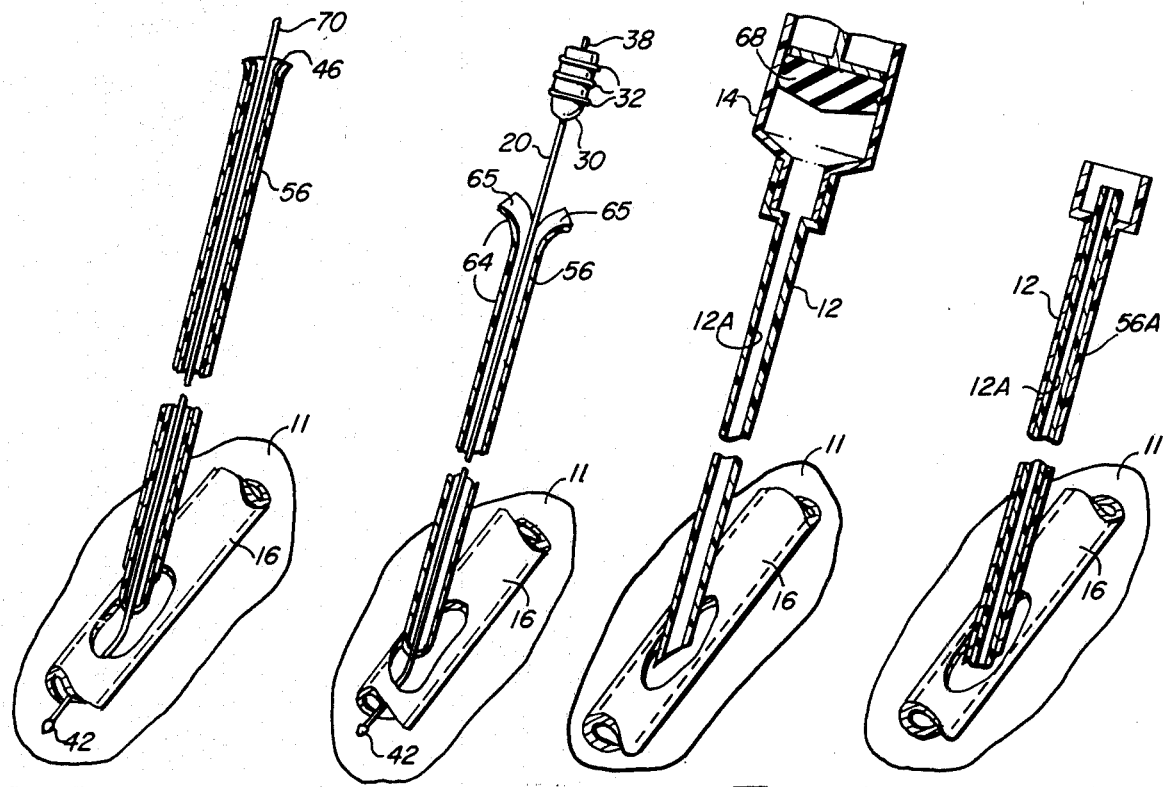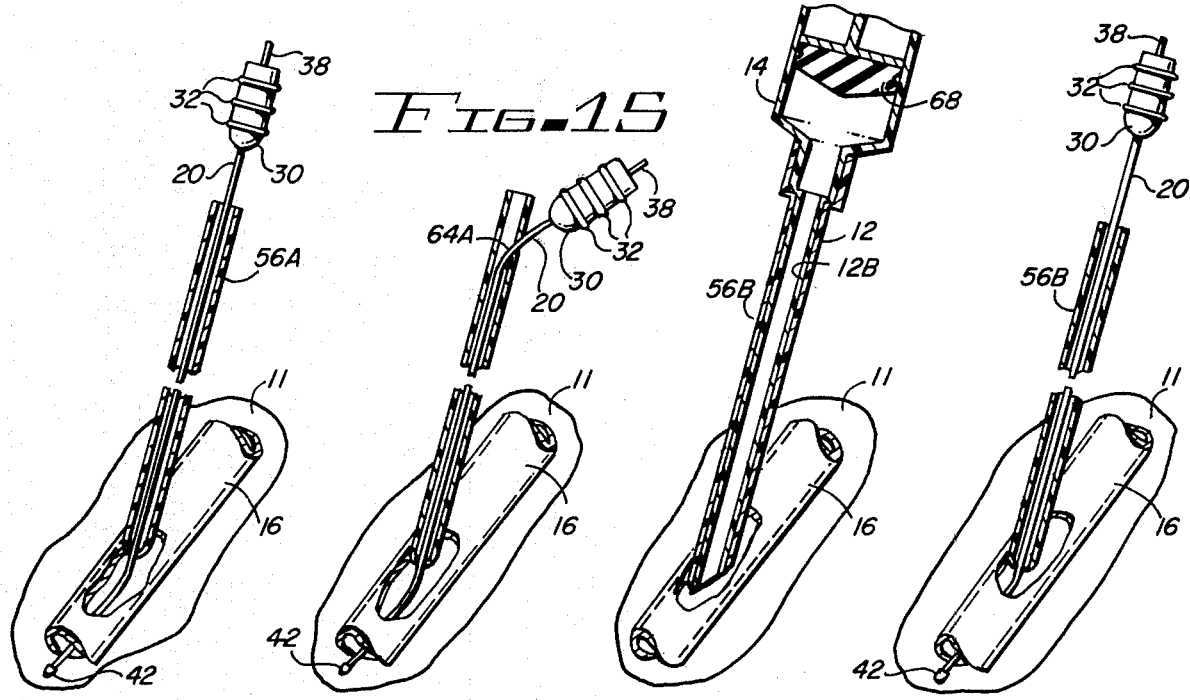

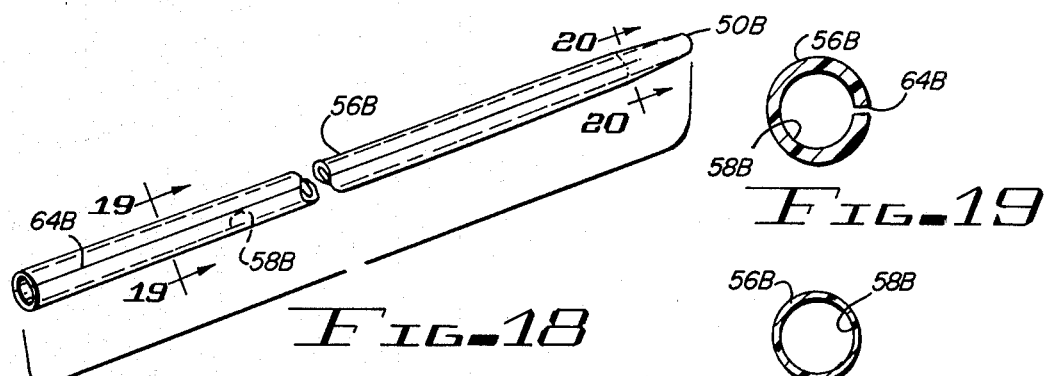
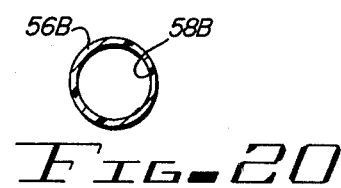
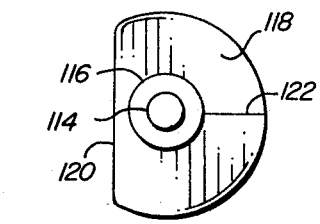
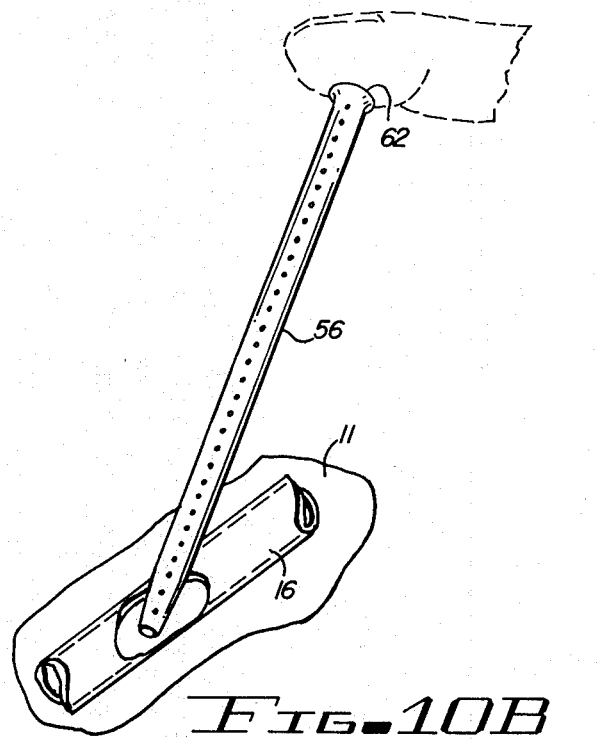
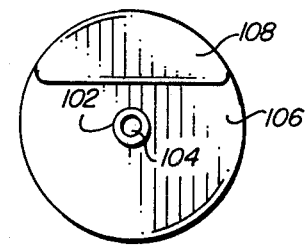
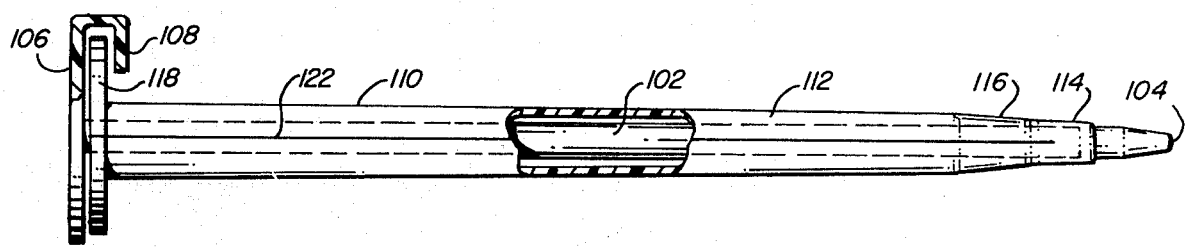

SPLIT SLEEVE INTRODUCERS FOR PACEMAKER ELECTRODES AND THE LIKE

This application is a division of application, Ser. No. 009,137, filed Feb. 5, 1979, now U.S. Pat. No. 4,243,050, in turn a continuation-in-part of application Ser. No. 860,246, filed Dec. 13, 1977, now U.S. Pat. No. 4,166,469.

BACKGROUND OF THE INVENTION

This invention relates to the surgical arts, and more particularly to apparatus and method for inserting pacemaker electrodes, catheters and similar devices into an internal organ or cavity of the human body.

The field of medical technology has experienced unprecedented developments in the last several decades. Some of the most dramatic advances in the medical field have occurred in the understanding and control of the human heart. The development of the pacemaker has solved some of the previous problems of heart disease and has extended the lives of thousands of patients.

In the past, the surgical implant of a pacemaker and permanent pacemaker electrode required approximately one to two hours. This surgical procedure was previously done by sectioning through the tissue layers of the patient down to the cephalic vein. An incision was made in the cephalic vein and the electrode tip inserted through the incision and through the vein into the right ventricle of the heart. The electrode was then tied to the body tissue and a second surface incision made for receiving the pacemaker pulse generator. The permanent electrode was connected to the pulse generator by a special plug-receptacle combination, and the pacemaker then was implanted within the patient.

The cephalic vein is located beneath the layers of the pectoralis muscle on the chest wall. Many times a large physical incision and a considerable amount of dissection is required to isolate the cephalic vein. Not infrequently, the cephalic vein is too small to accommodate the size of state-of-the-art pacemaker electrodes. In such a case, more extensive dissection must be made in following the cephalic vein to its origin. The cephalic vein extends beneath the clavicle, running ultimately to the subclavian vein.

It is also well known to insert temporary pacemaker electrodes into a patient's heart through the subclavian vein, using a surgical needle or conventional sheath introducer. The needle is introduced into a patient and the electrode tip is inserted through a center passage in the needle to enter an organ of the patient. The other end of the electrode is temporarily connected to an electronic device or the like.

Permanent pacemaker electrodes generally have an electrode tip on one end and an electrode plug, or hub, on the opposite end. Accordingly, a permanent pacemaker electrode cannot be inserted through a needle since the needle cannot be removed over the electrode plug.

In my U.S. Pat. No. 4,166,469 referred to above, I teach an apparatus and method for introducing a permanent pacemaker electrode into the heart through the subclavian vein by employing a sleeve and introducer combination, in which the sleeve has a slit, or weakened line, almost to the forward end of the sleeve. The unslit portion of the forward end prevents the sleeve from crimping as the sleeve passes through the hard tissue underneath the clavicle in the vicinity of the subclavian vein. Once the forward end of the sleeve is inside the subclavian vein, the electrode is passed through the sleeve and splits the unslit portion of the forward end. The sleeve may then be removed by gently sliding it out of the vein and peeling it off the electrode. If the unslit portion of the sleeve is not split during passage of the electrode down the sleeve, then the unslit portion may be easily slit as the sleeve is being peeled away from the electrode.

In my early work with respect to the apparatus and method described in my U.S. Pat. No. 4,166,469, I found that it was not desirable to slit the sleeve along its entire length, because a sleeve with a slit along its entire length tends to buckle or crimp around the slit at the forward end as it passes through the hard tissue layer surrounding the subclavian vein. Any structural deformity in the sleeve, such as a crimp, can tear the wall of the vein and injure the patient. Prior art which teaches sleeves pre-slit along the entire length include U.S. Pat. Nos. 3,459,184 and 3,185,152 to Ring.

There have also been suggestions in the literature for introducing permanent pacemaker electrodes through an unslit sleeve, and thereafter slitting the sleeve with the scalpel. See, for example, an article written by Drs. Friesen, et al., the *Canadian Journal of Surgery*, Volume 20, page 131, March, 1977; and Vellani, et al., *British Heart Journal*, Volume 31, page 106, 1969. However, in my early work, I found that the use of a scalpel in close proximity to the electrode created an unnecessary risk of damage to the insulation surrounding the electrode.

It has been recognized that electrode introduction through the subclavian vein gives rise to a potential risk of air embolism unless appropriate precautions are taken. The above-referenced article by Drs. Friesen, et al. disclose one solution to this potential problem which relies on careful breathing instructions to the patient. Frequently, however, pacemaker implant patients are elderly and are unable to follow the necessary breathing instructions.

In the split sleeve introducer described in my copending patent application, the sleeve slides independently of the introducer. There is a natural tendency to slide the sleeve forward from the introducer, as both structures are being inserted into the vein. If the sleeve is slid sufficiently forward, it is possible to move the sleeve an undesirable distance into the vein.

The use of the subclavian vein for the introduction of pacemaker electrodes is discussed in the following references: Mobin-Uddin, et al., *Journal of Thoracic and Card. Surgery*, pages 545-548 (1967); Jachuck, et al., *British Journal of Surgery*, Volume 61, pages 373-376 (1974); *Pacemaker Technology*, page 29 (1975); *Modern Cardiac Pacing*, page 78; Ahnlund, et al., *Annals of the Scandanavian Cardiology Congress, Copenhagen,* 1976; Sterz, et al.; *Wien. Med. Wschr.* 126, 28-31 (1976); Sterz, et al., *Z. Kardiol.*, Volume 66, pages 726-728 (1977); and Torresani, et al., *Stimucoeur,* Medical Supplement No. 21, Spring, 1978. Each of the above references also makes reference to earlier works of interest.

SUMMARY OF THE INVENTION

The present invention contemplates apparatus for introducing an object into the human body, and includes an introducer with a tapered end adapted to extend into the patient's body. A hollow sleeve formed of a tube is provided, the sleeve having a first portion with an inner dimension greater than the outer dimension of the introducer and a second porton at one end of the sleeve which extends parallel with the introducer and in close engagement therewith, with a gradual taper along the sleeve between the first and second portions. The sleeve has a longitudinal slit along the first portion, through the taper, and terminating short of the forward extremity of the sleeve.

In a preferred embodiment, means are provided for locking the sleeve with the introducer, such that the sleeve may be unlocked from the introducer by axial rotation of the sleeve with respect to the introducer. In accordance with a specific structural arrangement for providing the locking means, the sleeve includes a flange extending away from the sleeve a dimension which permits the flange to be engaged with a corresponding lip on a hub of the introducer. Additionally, the flange serves to provide a flat surface across which the physician can place his thumb to prevent the aspiration of air into the patient's body during the operation.

BRIEF DESCRIPTION OF THE DRAWINGS

FIG. 1 is an elevational view of an apparatus and method for implanting a pacemaker into the patient showing a needle being inserted through the exterior skin to puncture the subclavian vein to communicate with the heart of the patient;

FIG. 2 illustrates the completed implant of the pacemaker pulse generator and the pacemaker electrode in the patient;

FIG. 3 is an elevational side view of an introducer used to implant the electrode in the patient;

FIG. 4 is an elevational view of an introducer sleeve for use with the introducer shown in FIG. 3;

FIG. 5 is a front elevational view of a pacemaker pulse generator;

FIG. 6 is a side elevational view of the pulse generator shown in FIG. 5;

FIG. 7 is a view of the pulse generator shown in FIGS. 5 and 6 with a pacemaker electrode having an electrode tip and an electrode plug;

FIG. 8 illustrates the first step in the first method of introducing a permanent electrode into an internal organ of a patient wherein a needle punctures an internal vein of the patient;

FIG. 9 illustrates the second step of the first method showing a guide wire being introduced through the needle into the internal vein;

FIG. 10A illustrates the third step in the first method wherein the introducer and the introducer sleeve shown in FIGS. 3 and 4 are inserted into fluid communication with the internal vein;

FIG. 10B is the fourth step in the method, with the wire and introducer removed from the vein;

FIG. 11 is the fifth step of the first method wherein the electrode of FIG. 7 has been inserted through the introducer sleeve and the sleeve is being peeled off of the electrode to remove the sleeve over the plug at the end of the electrode;

FIG. 12 illustrates the first step of a second method of inserting the electrode into the patient wherein the needle is puncturing the internal vein of the patient;

FIG. 13 illustrates the second step of the second method wherein an introducer sleeve is inserted within the needle into fluid communication with the internal vein of a patient;

FIG. 14 illustrates the third step of the second method wherein the electrode is inserted through the introducer sleeve into the internal vein of the patient;

FIG. 15 shows the fourth step of the second method wherein the introducer sleeve is removed from the electrode;

FIG. 16 illustrates the first step of a third method of inserting the electrode into the patient wherein the needle and an introducer sleeve serially enter the internal organ of a patient;

FIG. 17 illustrates the second step of the third method wherein the electrode is inserted through the introducer sleeve upon removal of the needle;

FIG. 18 illustrates an alternate embodiment of the introducer sleeve of FIG. 4;

FIG. 19 is a sectional view along line 19—19 in FIG. 18;

FIG. 20 is a sectional view along line 20—20 in FIG. 18;

FIG. 21 is a side view of an introducer and sleeve combination in accordance with the present invention, and in which a portion of the sleeve is cut away;

FIG. 22 is a rear view of the sleeve of FIG. 21; and

FIG. 23 is a front view of the introducer of FIG. 21.

Similar reference characters refer to similar parts throughout the several views of the drawings.

DETAILED DESCRIPTION

FIG. 1 is an elevational view showing the insertion of a needle 12 and a syringe 14 with the needle 12 being inserted through the exterior skin 11 of a patient 10. The needle 12 pierces the subclavian vein 16 which leads directly to the heart 18 of patient 10. The subclavian vein is essentially inaccessible by surgical dissection. The subclavian vein is a large vein and readily receives a permanent pacemaker electrode. The insertion of the needle 12 is the first step in the method of implanting a pacemaker electrode with minimal incision to the patient.

FIG. 2 is an elevational view of the patient 10 with a pacemaker electrode 20 extending through the subclavian vein 16 to the heart 18. A pacemaker pulse generator 22 is shown implanted within the patient 10. The pulse generator 22 and the pacemaker electrode 20 are more fully shown in FIGS. 5-7.

The pulse generator 22 comprises an electronic circuit and power supply encapsulated in a covering 24 having an aperture 26. The pulse generator 22 includes a receptacle shown generally as a jack 28 for receiving a plug 30 of pacemaker electrode 20. The plug 30 comprises a plurality of O-rings 32 to seal with aperture 26 of covering 24. The pulse generator includes securing means for securing the plug 30 to jack 28 which is shown as a vice screw 34. The plug 30 is inserted within the receptacle jack 28 and the vice screw 34 is rotated for locking the plug 30 therein. A covering cap or plug 36 covers the end of aperture 26.

A connector pin 38 of plug 30 contacts the negative output of the pulse generator 22. A conductor 40 connects the connector pin 38 to an electrode tip 42 to provide a negative signal upon an output from the pulse generator 22. The positive terminal of the pulse generator 22 comprises an upper metallic electrode 44 shown in FIGS. 5-7. Although a specific example of the pacemaker pulse generator 22 and electrode 20 are used in this embodiment, it should be understood that the apparatus and method herein disclosed are not limited to such a pacemaker configuration. For example, the invention is compatible for use with an integral or one-piece pulse generator and electrode. The pulse generator 22 and the electrode 20 shown in FIGS. 5-7 are merely disclosed for clarifying the exact practice of the apparatus and method.

FIG. 3 illustrates an introducer 46 which is used in the method of inserting the pacemaker electrode 20 into the patient 10. The introducer 46 includes a through aperture 48 and a generally tapered tip portion 50. The introducer 46 also comprises a reinforced and flared base 52.

FIG. 4 illustrates a tubular introducer sleeve 56 having a through aperture 58, a flared flange 62 and a reduced sleeve wall tip 60. The introducer sleeve 56 and more particularly the aperture 58 is designed to closely fit the outer circumference of the introducer 46 with the base 62 abutting base 52 and the tip 60 tapering from the outer circumference of introducer 46. The introducer sleeve 56 also comprises severing means shown generally as 64 comprising a plurality of perforations to form a weakened line along the length of the introducer sleeve 56. Preferably, the perforations are indentations which do not extend completely through the sleeve 56, so that air does not flow through. The severing means may comprise a plurality of perforations, slots, or other weakening in one or more locations in the sleeve wall for enabling the sleeve to be severable along the length thereof. The severing means 64 may also comprise a precut in the sleeve wall along a portion of the introducer sleeve 56.

FIGS. 3-11, inclusive, illustrate the first through fifth steps of the method of inserting the electrode 20 into an internal organ shown as the subclavian vein 16.

FIG. 8 illustrates the needle 12 puncturing the exterior skin 11 of the patient 10 to enter the vein 16. It is particularly suitable in accordance with the present invention to employ an 18 gauge, thin wall needle. A piston 68 of syringe 14 is withdrawn slightly to draw a small quantity of blood from vein 16 to insure that the needle 12 has entered the vein 16. The blood may be returned into the vein 16 and the syringe 14 removed from needle 12 as shown in FIG. 9. A flexible guide wire 70, preferably of the J-wire type, has a diameter sufficiently small to enter through the internal passage 12A of needle 12. The guide wire 70 is pushed through needle 12 to enter the vein 16 as shown in FIG. 9. The needle 12 is then removed enabling the introducer 46 and the introducer sleeve 56 to be guided along guide wire 70 to enter the vein 16 as shown in FIG. 10A. The base 62 of the sleeve 56 abuts base 52 of introducer 46. The length of sleeve 56 is less than the length of introducer 46 as shown in FIGS. 3, 4 and 10A. The introducer 46 adds mechanical strength to the introducer sleeve 56 during entry in the patient 10. The guide wire 70 and introducer 46 are then removed from the vein 16 leaving the introducer sleeve 56 in fluid communication with the vein 16, as shown in FIG. 10B. The physician then places his thumb across the flange 62, to prevent air from being aspirated into the vein 16 while the electrode 20 is being prepared for insertion (Note FIG. 10B). The pacemaker electrode tip 42 is then lubricated, and inserted into introducer sleeve 56 to enter vein 16. The electrode 20 is pushed until the electrode tip 42 enters the heart 18 as shown in FIG. 2. The sleeve 56 is severed along the severing means 64 and concomitantly withdrawn from the patient 10 leaving the electrode tip 42 within the heart cavity. In the case of the sleeve 56 being precut, the sleeve is merely peeled off at the electrode 20. The electrode plug 30 may then be connected to the pulse generator 22. The pulse generator 22 is then implanted into the patient 10. As shown in FIG. 11, in the case where the sleeve 56 is perforated to form the weakened line 64, the sleeve may be peeled slightly away at the flange 62 to form tabs 65 which may be used to grasp and peel away the sleeve while removing from the vein 16. The tabs 65 may be formed by peeling a portion of the sleeve 56 back prior to insertion in the vein 16; however it is preferable to do so after insertion of the electrode 20, in order that the flat opening of flange 62 may be employed to prevent the aspiration of air into the vein 16, as described above with respect to FIG. 10B.

FIGS. 12-15 show the first four steps of a second method of introducing the electrode 20 into an internal organ of a patient. FIG. 12 illustrates the needle 12 puncturing the external skin 11 to enter the vein 16 in a manner similar to FIG. 8. The piston 68 is withdrawn drawing blood from vein 16 to insure proper entry into the vein 16. The syringe 14 is then removed enabling a sleeve 56A to be inserted within the internal passage 12A of needle 12 to enter the vein 16. The sleeve 56A is substantially tubular and having severing means 64A similar to that shown in FIG 4. The introducer sleeve 56A does not have an expanded base 62 as in FIG. 4 which enables the needle 12 to be withdrawn over the sleeve 56A leaving the sleeve 56A within vein 16. The electrode tip 42 is inserted through the introducer sleeve 56A into the vein 16 to enter heart 18 as shown in FIG. 14. The sleeve 56A may then be removed by severing along the severing means 64A as shown in FIG. 15. The limitation of the second method shown in FIGS. 12-15 is determined by the state-of-the-art size of the electrode tip 42 shown in FIGS. 7, 14 and 15. The size of the needle used is determined by the size of the electrode tip 42. Large electrode tips require a large needle which can produce substantial tissue damage. In such a case, the first method shown in FIGS. 8-11 is preferable since the introduction of the introducer and introducer sleeve 46 and 56 as shown in FIG. 10 merely separates tissue from the original incision by needle 12 rather than cutting of the tissue. Accordingly, a smaller needle is required in the first method shown in FIGS. 8-11 than the second method shown in FIGS. 12-15.

FIGS. 16 and 17 illustrate the first and second steps of a third method of inserting a pacemaker electrode into a vein 16. In this embodiment, the introducer sleeve 56B more fully shown in FIGS. 18-20 comprises a central through aperture 58B and a tip portion 50B. FIGS. 19 and 20 illustrate sectional views of the introducer sleeve 56B showing the relative wall thicknesses at section lines 19—19 and 20—20 in FIG. 18. The severing means 64B in this embodiment comprises a cut extending from the end 62B of introducer sleeve 56 to a region with approximately five millimeters of tip 50B.

The inner aperture 58B of sleeve 56B is selected to closely receive the outer surface 12B of needle 12. The length of introducer sleeve 56B is slightly shorter than the length of needle 12 enabling the needle to make a primary puncture through the external skin 11 of the patient 10 and internal organs prior to entry by the introducer sleeve 56B. The needle 12 and sleeve 56B are inserted into communication with the vein 16 and the needle 12 is withdrawn, leaving the sleeve 56B in communication with the vein 16. The electrode 20 may then be inserted into the vein 16 and the heart 18 by the introducer sleeve 56B as shown in FIG. 17. The connector plug 30 may then be secured to the pulse generator 22 as heretofore described. In this embodiment, the needle required is larger than the method shown in FIGS. 8-11, but is generally smaller than the needle required in FIGS. 12-14. In this case, the sleeve 56B closely fits on the outer surface 12B of needle 12.

A third embodiment of the sleeve and introducer arrangement is shown in FIGS. 21-23. The introducer 102 includes a tapered forward end 104 and a through aperture (not shown) adapted to receive the guide wire 70.

The introducer 102 includes a hub 106 at the rearward end, the hub including a lip 108 overlapping in the forward direction of the introducer (Note FIG. 23).

The tubular sleeve 110 is formed of two portions, a first portion 112 having an inner dimension greater than the outer dimension of the introducer 102 and being slightly tapered from, for example, a 13 French to an 11 French of the forward end of the first portion 112; and a second, cylindrical portion 114 which extends parallel to, and in close engagement with the outer periphery of the introducer 102. The sleeve 110 further includes a gradual taper 116 along its length between the first and second portions 112, 114. The forward end of the second portion 114 is rounded to prevent crimping or tearing during entry into the vein 16.

The sleeve 110 further includes a flange 118 at its rearward end, the flange having a flat 120 along its periphery corresponding to the dimension and shape of the lip 108 of the introducer 102, so as to permit the flange to be pushed under the lip by first axially sliding and then rotating the sleeve. This permits the sleeve 110 to be locked to the introducer 102 during the step of sliding the two together along the wire 70 (FIG. 10A) and avoids inadvertent movement of the sleeve ahead of the introducer.

The sleeve 110 further includes a slit 122 extending through the flange 118 (FIG. 22), along the first portion 112 and through the taper 116. Preferably, the cylindrical, parallel second portion 114 of the sleeve 110 is between one to five millimeters long, with the slit 122 extending the taper 116, and terminating in the second portion 114.

The introducer 102 and sleeve 110 are used in the manner described above with reference to FIGS. 8-11 and 16-17. As the electrode 20 is passed through sleeve 110 while in the vein 16, the tip 42 splits the unslit forward end of the first portion 114. If the type of electrode being introduced does not have a tip 42 of sufficient size to split the unslit forward end, then this is easily accomplished during the step of peeling the sleeve 110 away from the electrode 20, in the manner shown in FIG. 11. As was described above, it is preferred that the sleeve 110 be formed of a radio-opaque polypropelene.

The foregoing has described three distance methods of inserting the electrode 20 into an internal organ of the patient 10. In each case, an electrode sleeve 56 was used for introducing the electrode 20 into an internal organ of the patient 10. Mechanical strength is given to the introducer sleeve during entry into the patient 10. In the first method, the introducer aids entry of the sleeve. In the second and third methods, the needle aids entry of the sleeve. Accordingly, the introducer sleeve may be made of a lightweight material and preferably comprises a radio-opaque polypropelene. The physical characteristics of the sleeve shown in FIGS. 4, 18-20 or 21-23 may be adapted to any of the three methods.

The apparatus described includes the interrelation of structural sizes of the needle, introducer sleeves and introducers. The severing means includes a structure for enabling of the sleeve to be peeled off of the electrode. The severing means may take various forms such as perforations, holes, through cuts, reduced wall thickness and integral cutting agents such as strings and the like.

The method of the invention comprise the introduction of an introducer sleeve by various means. The pacemaker electrode is then inserted into the internal organ through the introducer sleeve, only a portion of which is weakened. The sleeve is then peeled off along the weakened line of the sleeve to remove the sleeve over the electrode plug. In the apparatus as set forth herein, the sleeve comprises severing means for enabling the severing of the sleeve along the length.

I claim:

1. Apparatus for introducing an object into the human body, said apparatus comprising:
   a tubular introducer with a tapered end adapted to extend into said body;
   a hollow sleeve surrounding the introducer and formed of a tube having a first portion with an inner dimension greater than the outer dimension of said introducer and a second portion at one end of said sleeve which extends parallel with said introducer, said second portion dimensioned for close engagement with said introducer adjacent the tapered end thereof, with a gradual taper along said sleeve between said first and second portions; and
   said sleeve having a longitudinally weakened line along said first portion from the other end of said sleeve, said weakened line extending through said taper and terminating short of said one end.

2. The apparatus recited in claim 1 wherein said parallel, second portion of said sleeve is between 1-5 millimeters in length.

3. The apparatus recited in claim 1 wherein said longitudinally weakened line extends along said taper between said first and second portions of said sleeve.

4. The apparatus recited in claim 1 wherein said sleeve is formed of polypropylene.

5. The apparatus recited in claim 1 further comprising means for locking said sleeve with said introducer.

6. The apparatus recited in claim 1 wherein said first portion of said sleeve further comprises a flange at the other end thereof, said flange having an outward dimension away from said sleeve to permit thumb placement across said flange to prevent air flow through said sleeve.

7. The apparatus recited in claim 6 further comprising means for locking said flange to said introducer.

8. The apparatus recited in claim 1 wherein said sleeve is radio-opaque.

9. The apparatus recited in claim 1 further comprising:
   a needle adapted to extend into the subclavian vein; and
   a flexible wire having a dimension permitting said wire to be inserted through said needle and said introducer, said wire dimensioned to slide through said introducer.

10. Apparatus for introducing a pacemaker electrode or the like into a subclavian vein of a patient, said apparatus comprising:
    a small, hollow needle, on the order of about 18 gauge, adapted to be inserted into said subclavian vein;
    a flexible wire dimensioned to extend through said needle and into said vein;

an introducer formed of a hollow tube having an inner dimension so as to receive said wire therein and a tapered forward end for extension into said subclavian vein;

a hollow sleeve formed of a tube having a first portion with an inner dimension greater than the outer dimension of said introducer and a second portion at the forward end of said sleeve which extends parallel with said introducer and in close engagement therewith at said tapered end of said introducer, with a gradual taper between said first and second portions of said sleeve;

said sleeve having a longitudinal slit extending along said first portion from the end opposite said forward end and through said taper, and terminating short of the extremity of said sleeve in said second portion; and wherein said electrode may be introduced into the subclavian vein of said patient by inserting said needle into the vein, inserting said wire through said needle into the vein, removing said needle and sliding said introducer with said sleeve thereon together along said wire and into said vein, removing said wire and said introducer, inserting said electrode through said sleeve and into the vein, thereafter pulling said sleeve from the vein and peeling said sleeve away from said electrode along said longitudinal slit, and tearing the unslit second portion of said sleeve along said longitudinal slit in the event that said second portion is not torn by passage of said electrode therethrough.

* * * * *